(12) United States Patent
Wallace et al.

(10) Patent No.: US 8,203,030 B2
(45) Date of Patent: Jun. 19, 2012

(54) TRANSGENIC MOUSE MODELS FOR DISEASES CAUSED BY MTDNA MUTATIONS AND RELATED METHODS

(75) Inventors: Douglas C. Wallace, Irvine, CA (US); Wei Wei Fan, Aliso Viejo, CA (US); Katrina G. Waymire, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 374 days.

(21) Appl. No.: 12/205,588

(22) Filed: Sep. 5, 2008

(65) Prior Publication Data

US 2010/0169985 A1    Jul. 1, 2010

Related U.S. Application Data

(60) Provisional application No. 60/970,227, filed on Sep. 5, 2007.

(51) Int. Cl.
*G01N 33/00* (2006.01)
*A01K 67/00* (2006.01)
*A01K 67/027* (2006.01)

(52) U.S. Cl. .................................. 800/18; 800/3; 800/9

(58) Field of Classification Search ................. 800/3, 9, 800/18
See application file for complete search history.

(56) References Cited

U.S. PATENT DOCUMENTS 5,494,794 A * 2/1996 Wallace ............................ 435/6

OTHER PUBLICATIONS

Sligh, J. E., et al. (2000, Proc. Natl. Acad. Sci. USA 97:14461-14466.*
Inoue, K. et al., 2000, Nature Genetics 26: 176-181.*
Kasahara et al, 2006, Hum Molec Genet 15:871-881.*
Douglas C. Wallace, "A Mitochondrial Paradigm of Metabolic and Degenerative Diseases, Aging, and Cancer: A Dawn for Evolutionary Medicine", Annual Review of Genetics, 2005, vol. 39, pp. 359-407.
Wallace et al., "Familial Mitochondrial Encephalomyopathy (MERRF): Genetic, Pathophysiological, and Biochemical Characterization of a Mitochondrial DNA Disease", Cell, vol. 55, No. 4, pp. 601-610, Nov. 18, 1988, Copyright 1988 by Cell Press.
Shoffner et al., "Myoclonic Epilepsy and Ragged-Red Fiber Disease (MERRF) is Associated with a Mitochondrial DNA tRNA Lys Mutation", Cell, vol. 61, No. 6, pp. 931-937, Jun. 15, 1990, Copyright 1990 by Cell Press.

Heddi et al., "Mitochondrial DNA Expression in Mitochondrial Myopathies and Coordinated Expression of Nuclear Genes Involved in ATP Production", Journal of Biological Chemistry, vol. 268, No. 16, Issue of Jun. 5, pp. 12156-12163, 1993.
Shoffner et al., "Mitochondrial DNA Variants Observed in Alzheimer Disease and Parkinson Disease Patients", Genomics vol. 17, pp. 171-184 (1993).
Li et al., "Dilated Cardiomyopathy and neonatal Lethality in Mutant Mice Lacking Manganese Superoxide Dismutase", Nature Genetics, vol. 11, No. 4, pp. 376-381, Dec. 1995.
Graham et al., "A Mouse Model for Mitochondrial Myopathy and Cardiomyopathy Resulting from a Deficiency in the Heart/Muscle Isoform of the Adenine Nucleotide Translocator", Nature Genetics, vol. 16, No. 3, pp. 226-234, Jul. 1997.
Sligh et al., "Maternal Germ-Line Transmission of Mutant mtDNAa from Embryonic Stem Cell-Derived Chimeric Mice", Proceedings of the National Academy of Sciences of the United States of America (PNAS), Dec. 19, 2000, vol. 97, No. 26, pp. 14461-14466.
Fan et al., "A Mouse Model of Mitochondrial Disease Reveals Germline Selection Against Severe mtDNA Mutations", Science Feb. 15, 2008, vol. 319(5865), pp. 958-962.
Inoue et al., "Generation of Mice with Mitochondrial Dysfunction by Introducing Mouse mtDNA Carrying a Deletion into Zygotes", Nature Genetics, vol. 26, No. 2, Oct. 2000, pp. 176-181.
Kasahara et al., "Generation of Trans-Mitochondrial Mice Carrying Homoplasmic mtDNAs with a Missense Mutation in a Structural Gene using ES Cell", Human Molecular Genetics, 2006, vol. 15, No. 6, pp. 871-881, Epub Jan. 31, 2006.
Wallace et al., "Mitochondrial DNA Mutation Associated with Leber's Hereditary Optic Neuropathy", Science, vol. 242(4884), pp. 1427-1430, Dec. 9, 1988.

* cited by examiner

*Primary Examiner* — Valarie Bertoglio
*Assistant Examiner* — David A Montanari
(74) *Attorney, Agent, or Firm* — Robert D. Buyan; Stout, Uxa, Buyan & Mullins

(57) ABSTRACT

Animal models and methods wherein homoplasmic and heteroplasmic mtDNA mutation(s) are induced in an animal (e.g., a mouse) to cause or facilitate the development of a disorder (e.g., disease, malformation, defect, abnormality or other disorder). In at least some embodiments, the mtDNA mutation(s) will cause or facilitate the development of an age-related disorder, such as a cardiac disease, cardiomyopathy, muscle disease, cancer, abnormaly in tissues of high cellular turnover, heart dysfunction, graying of hair, alopecia, auditory function loss, cochlear degeneration, immune cell loss, anemia, male germ cell loss leading to lack of sperm and infertility, skeletal muscle mass loss (sarcopenia), neurodegeneration, increased presence of apoptotic markers, and loss of bone mass.

9 Claims, 17 Drawing Sheets

Control　　　　　　　　　　　MUT
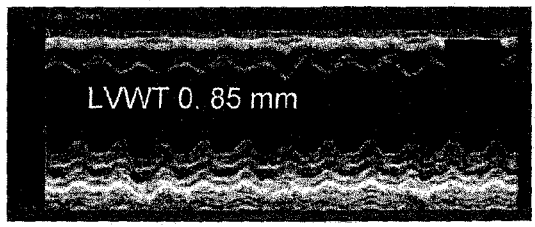 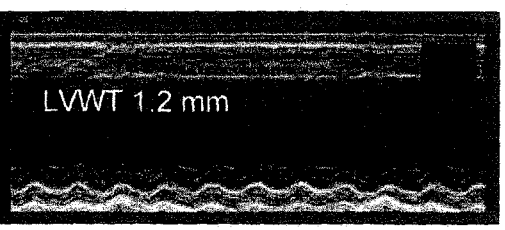
Fig. 6　　　　　　　　　　　Fig. 6A
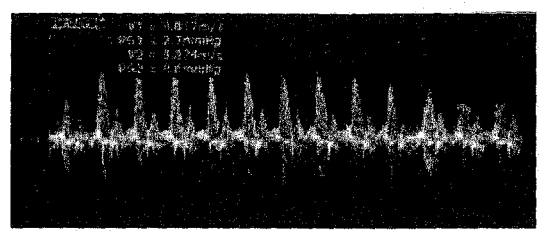 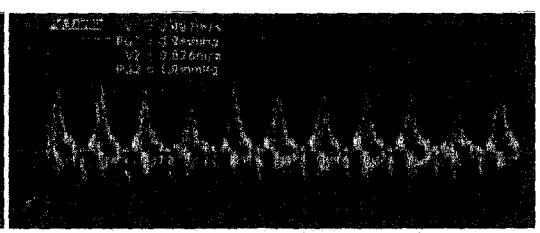
Fig.6B　　　　　　　　　　　Fig. 6C
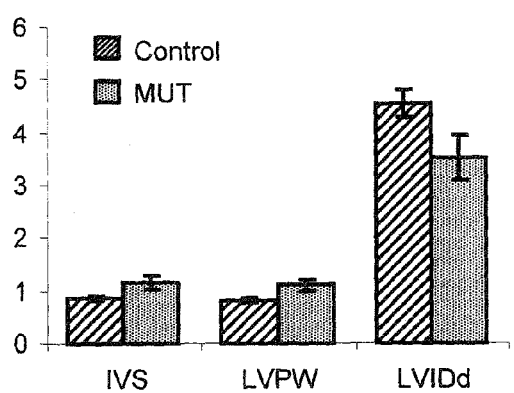 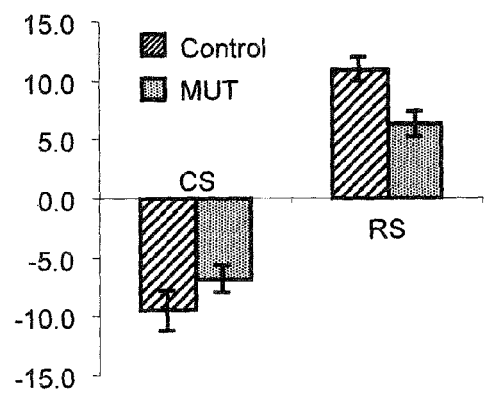
Fig. 6D　　　　　　　　　　　Fig. 6E

TRANSGENIC MOUSE MODELS FOR DISEASES CAUSED BY MTDNA MUTATIONS AND RELATED METHODS

RELATED APPLICATION

This patent application claims priority to U.S. Provisional Patent Application No. 60/970,227 filed Sep. 5, 2007, the entire disclosure of which is expressly incorporated herein by reference.

STATEMENT REGARDING GOVERNMENT SUPPORT

This invention was made with Government support under Grant Nos. NS021328, AG013154, AG024373 and DK073691, awarded by the National Institutes of Health. The government has certain rights in this invention.

FIELD OF THE INVENTION

The present invention relates generally to genetics and biomedical methodology and more particularly to the establishment and uses of a mouse model of disorders (e.g., age-related disorders, cardiac disease, muscle disease, cancer, etc.) caused by a mitochondrial DNA point mutation.

BACKGROUND

Mitochondrial DNA (mtDNA) base substitution mutations are believed too be a common cause of age-related degenerative diseases as well as cancer. However, no mouse model has been generated in which a mtDNA base substitution has been stably introduced into the mouse germline and resulted in an inherited predisposition to and age-related disease or cancer. We now report the introduction of a mtDNA harboring a missense mutation in the COI gene into the mouse that predisposes the mice to develop myopathy and hypertrophic cardiomyopathy as well as certain hyperproliferative conditions in an age-related manner.

United States Patent Application Publication No. 2007/0022488 (Prolla et al.) entitled "Mouse Model for Aging" describes a mouse model for mammalian aging comprising a transgenic mouse having a genomic mtDNA mutation. In one embodiment, this mouse model comprises a mouse having a genomic mutation in the exonuclease domain II (ExoII) of a mitochondrial DNA polymerase gamma (POIG) gene, wherein the mutation leads to high levels of mutations in polymerase mtDNA. The entire disclosure of United States Patent Application Publication No. 2007/0022488 (Prolla et al.) is hereby expressly incorporated herein by reference.

As early as 2005, Applicants had shown that base substitution mutations in the human mtDNA can result in age-related myopathy, cardiomyopathy, and neuropathy (Wallace D. C., 2005. *Annual Rev Genet* 39:359-407) and that missense mutations in the mtDNA COI gene are associated with increased risk for prostate cancer (Petros, J. A., et al., 2005. *Proc. Natl. Acad. Sci.* 102: 719-724).

Three publications are known to have previously reported the introduction of mtDNA variants into the mouse germline. In the first report, which was from Applicant's laboratory, a base substitution in the mtDNA 16S rRNA was introduced into the moue germline. However, this mutation proved to be too severe and all of the mutant mice died before they could reproduce and transmit the mutation to subsequent generations Sligh, J. E., et al, 2000, *Proc. Natl. Acad. Sci. USA* 97:14461-14466. The second paper reported the introduction of a heteroplasmic (mixed mutant and wild type) mtDNA deletion mutation into the mouse germline. While the mutant mtDNA was transmitted through the female germline in the heteroplasmic state, the deleted mtDNA also segregates. Hence, this mutation was not stable and the phenotype was not consistent. Inoue, K. et al., 2000, Nature Genetics 26: 176. The third paper reported the introduction of the same COI mutation into the mouse germline that we declare here. However, these authors declared that the mice had no phenotype, probably because they did not understand that mitochondrial pathologies generally have a delayed onset and progressive course. Kasahara A et al, 2006, *Hum Molec Genet* 15:871.

There remains a need in the art for the development of additional devices and methods for controlling the depth or positioning of needles, cannulae and other diagnostic/therapeutic devices within the walls of organs or other tissue masses.

SUMMARY OF THE INVENTION

The present invention generally provides a transgenic animal (e.g., mouse) model for a disorder caused by a mitochondrial DNA point mutation, said mouse model comprising an animal (e.g., a mouse) that has a mtDNA missense mutation that causes or facilitates the development of the disorder. In some embodiments the mouse may have a homoplasmic mtDNA missense mutation while in other embodiments the mouse may have a heteroplasmic mtDNA missense mutation. In some embodiments, the disorder may be selected from the group consisting of: cardiac disease, cardiomyopathy, muscle disease, cancer, abnormalities in tissues of high cellular turnover, heart dysfunction, graying hair, alopecia, auditory function loss, cochlear degeneration, immune cell loss, anemia, male germ cell loss leading to lack of sperm and infertility, skeletal muscle mass loss (sarcopenia), neurodegeneration, increased presence of apoptotic markers, and loss of bone mass.

In accordance with the present invention, there is provided a transgenic mouse of the foregoing character that has an mtDNA ND6-COI double mutation.

Further in accordance with the present invention, there is provided a transgenic mouse of the foregoing character wherein the disorder is hypertrophic cardiomyopathy and wherein the mouse is a homoplasmic COI T6589C missense mutant mouse. This transgenic mouse may, in some embodiments, have mtDNA that is homoplasmic for a COI missense mutation (T6589C), 50-50 heteroplasmic for an ND6 C insertion frameshift mutation (13885insC) and has a T deletion reversion of that mutation (13885insCdelT). Also, in some embodiments, this mouse may be female and may be backcrossed to C57BL/6J males.

Still further in accordance with the present invention, there is provided a method for determining potential effectiveness of a test therapy in treating, delaying the onset of or lessening the severity of a disorder that is caused or facilitated by an mtDNA missense mutation, such method comprising the steps of (A) providing an animal (e.g., a mouse) in whom an mtDNA missense mutation that causes or facilitates the development of the disorder has been induced (as summarized above), (B) administering the test therapy to the animal and (C) determining whether the test therapy was effective in treating, delaying the onset of or lessening the severity of the disorder itself, or of a symptom of the disorder, compared to an untreated animal. In this method, the test therapy may comprise any type of test therapy, including but not necessarily limited to, a drug, a chemical or other composition of matter, a biologic, a vaccine, a therapeutic device, etc.

Further aspects, details and embodiments of the present invention will be understood by those of skill in the art upon reading the following detailed description of the invention and the accompanying drawings.

BRIEF DESCRIPTION OF THE DRAWINGS

FIGS. 1A and 1B show sequences of the homoplasmic COI T6589C missense (V421A) (conservation index=100%) and the ND6 13885insC frameshift mutations and their wild type counterparts; FIG. 1C shows respiration analysis of mitochondria from LM(TK−) and LMJL8 cells indicating no complex I (Glutamate+Malate) dependent respiration and 43% increased complex II (succinate) dependent respiration; FIG. 1D shows OXPHOS enzyme analysis of LM(TK⁻) and LMJL8 cells revealed no complex I activity, a 91% increased complex II+III activity, and a 62% increased complex IV activity, all values normalized to citrate synthase; FIG. 1E shows sequences of the ND6 13885insC frameshift and 13885insCdelT revertant mtDNAs derived from two EC77 clones and FIG. 1F shows primer extension analysis of four ES cell cybrids revealed the presence of the ND6 1388insCdelT revertant mtDNA in EC77 at 4%.

FIG. 2A shows mtDNA genotypes of chimeras CH1, CH2, and CH3 tissues and FIG. 2B shows percentages of the ND6 13885insC frameshift mutation in tails of EC77-AG and its offspring, the frameshift mutation was lost within 4 generations.

FIG. 3A shows the sequence of the EC77-AG tail mtDNA and the percentage of 13885insC calculated from cloning and sequencing analysis, FIG. 3B shows primer extension analysis of the percentages of the ND6 13885insC and ND6 13885insCdelT mutations in EC77-AG tissues, FIG. 3C shows mitochondrial OXPHOS enzyme activities in EC77-AG tissues relative to 129×B6 control tissues (wherein complex I activity was reduced 33% in brain, 10% in heart, 17% in liver and 20% in skeletal muscle), FIG. 3D shows mitochondrial complex IV activity of EC77-AG tissues relative to 129×B6 control tissues (wherein Complex IV was reduced 56% in brain and 46% in skeletal muscle, but increased 19% in heart and 39% in liver) and FIG. 3E shows primer extension analysis of the ND6 13885insC frameshift and 13885insCdelT revertant mtDNAs in 12 individual oocytes.

FIG. 4A is a micrograph of heart tissue from a 12-month-old control B6 mouse with normal mitochondria (x3200), FIG. 4B is a micrograph of skeletal muscle from a 12-month-old control B6 mouse also showing normal mitochondria (x3200), FIG. 4C is a micrograph of heart tissue from the EC77-AG founder mouse harboring 47% ND6 13885insC and 100% COI T6589C mtDNAs showing intramitochondrial lipid droplets (arrows) (x1650), FIG. 4D is a micrograph of skeletal muscle from EC77-AG showing decreased mitochondrial matrix density and cristolysis (thin arrow) and myelin-like inclusions (thick arrow) (x2100), FIG. 4E is a micrograph of heart tissue from a N2 mouse EC77 #4 harboring 14% ND6 13885insC and 100% COI T6589C mtDNAs showing mitochondrial proliferation (arrow) (x2700), FIG. 4F is a micrograph of heat tissue from another N2 mouse EC77 #9 harboring 14% ND6 13885insC and 100% COI T6589C mtDNAs exhibiting two mitochondria inside a membrane bound vacuole (arrow) (x2100), FIG. 4G is a micrograph of heart tissue from EC77 #4 with 14% ND6 13885insC and 100% COI T6589C mtDNAs revealing focal loss of myofilaments (arrow) (x2100), FIG. 4H is a micrograph of heart tissue from a N3 mouse EC77 #36 harboring 0% ND6 13885insC and 100% COI T6589C mtDNAs exhibiting diffuse loss of myofilaments (arrows) (x3200) and FIG. 4I is a micrograph of heart tissue from EC77 #36 with mitochondrial proliferation, decreased mitochondrial matrix and cristolysis (arrows) (x2100).

FIG. 5A shows that Complex I activities in various tissues demonstrate no significant reductions except for in the muscle of the 14% frameshift mtDNA mouse, FIG. 5B shows that Complex II+III activities in tissues were minimally affected in any of the genotypes and FIG. 5C shows that Complex IV activities among tissues were reduced 40%-60% in all mtDNA mutant mice relative to B6 controls ($p \ll 0.0001$). n=6 (B6), 7 (0% 13885insC and 100% T6589C), 3 (6% 13885insC and 100% T6589C), and 4 (14% 13885insC and 100% T6589C).

FIGS. 6A-6F show echocardiograms and relate graphic data demonstrating that hypertrophic cardiomyopathy in one year old mice harboring mtDNAs that were homoplasmic for the COI T6589C missense mutation on the ND6 13885insCdelT revertant background (n=7) relative to age-matched B6 controls (n=5) as described in Example 1 below. Specifically, FIG. 6A is a representative control heart echocardiogram showing normal left ventricular wall thickness (LVWT) at both inter ventricular septum (IVS) and left ventricular posterior wall (LVPW) on an M-mode echocardiogram, FIG. 6B is a representative mutant heart echocardiogram exhibiting hypertrophied LVWT at the same level of LV as demonstrated in A, FIG. 6C shows a normal mitral valve inflow pattern: E/A ratio=2.2, FIG. 6D shows an abnormal mitral inflow pattern: E/A ratio=0.72 revealing diastolic dysfunction and FIGS. 6E and 6F show quantitative echocardiographic data of LVWT, circumferential strain (CS) and radial strain (RS). Wild type (WT) n=5, COI mutant (MT) n=7; LVWT in mm, WT=0.86±0.0, MT=1.16±0.1 (P<0.001); LVIDd in mm, WT=4.54±0.3, MT=3.51±0.5 (P<0.001); Left ventricular ejection fraction (LVEF) in %, WT=70±7, MT=75±4; E/A, WT=1.7±0.7, MT=1.7±0.7; Rotation in degrees, WT=1.1±0.1, MT=1.4±0.3; CS in %, WT=−9.5±1.7, MT=−6.8±1.1 (P<0.001); RS in %, WT=10.9±1, MT=6.3±1.1 (P<0.001).

DETAILED DESCRIPTION

Figure 1:
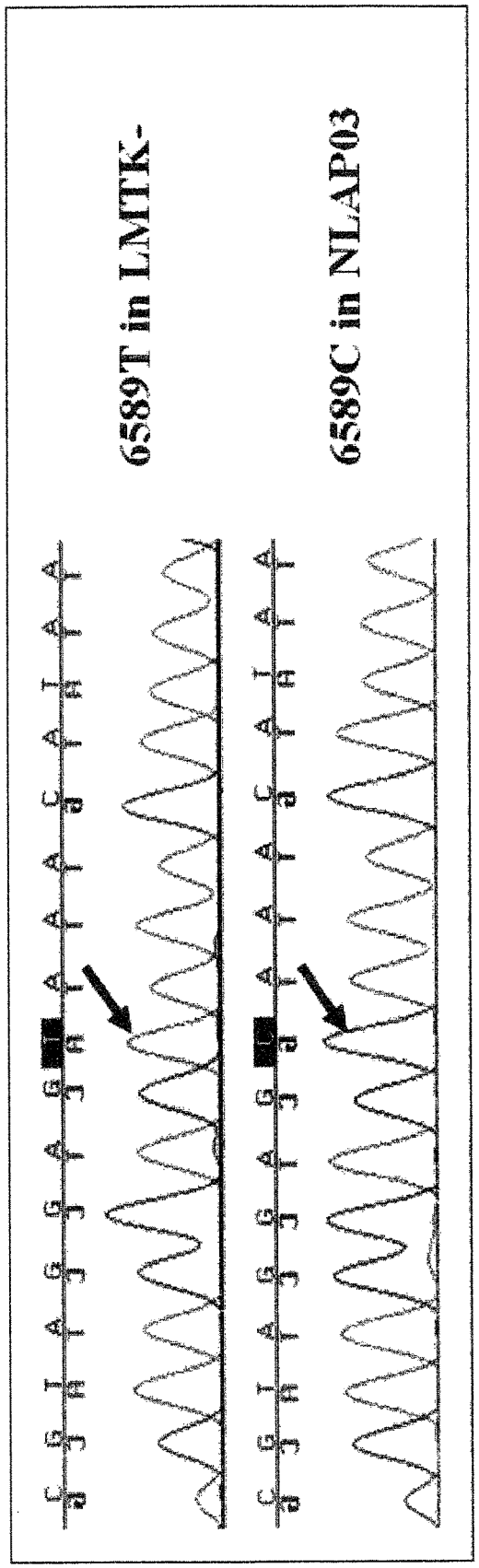
FIGS. 1A-1F show analysis of the mtDNAs and mitochondria of the LMJL8 and ES cybrids harboring the COI T6589C and ND6 13885insC double mtDNA mutant as described in Example 1 below.

The following detailed description and the accompanying drawings are intended to describe some, but not necessarily all, examples or embodiments of the invention. The contents of this detailed description and accompanying drawings do not limit the scope of the invention in any way.

The present invention provides mouse models comprising mice having homoplasmic and heteroplasmic mtDNA mutation(s) which cause or facilitate the development of a disorder (e.g., disease, malformation, defect, abnormality or other disorder). In at least some embodiments, the mutation(s) will cause or facilitate the development of an age related disorder. Examples of age-related disorders that have been reported to be associated with mtDNA mutations include but are not limited to: cardiac diseases, muscle diseases, cancers, abnormalities in tissues of high cellular turnover, heart dysfunction, graying hair and alopecia, auditory function loss, cochlear degeneration, immune cell loss, anemia, male germ cell loss leading to lack of sperm and infertility, skeletal muscle mass loss (sarcopenia), neurodegeneration, increased presence of apoptotic markers, and loss of bone mass.

The mouse models of the present invention will permit the demonstration of the central role that the mitochondria play in the pathophysiology of age-related degenerative disease as well as cancer. This may reveal specific therapeutic targets for intervening in these diseases. These same mice can then be used to test the efficacy of these therapeutics. The potential commercial uses of the mice of the present invention include but are not limited to screening for the toxicity and efficacy of preventative therapeutics for age-related degenerative disease and cancer.

In addition to the information set forth herebelow, additional details, elements and aspects of the present invention will be understood by those of skill in the art upon reading Appendix A, which is expressly included in and forms a part of the specification of this provisional patent application.

Homoplasmic Mouse Model

Applicants isolated a cultured mouse cell line which harbored a COI gene missense mutation (T6589C, V421A, conservation index ~100%), used our cybrid technique to transfer the mutations into our female mouse embryonic stem (ES) cell line, and introduced the mtDNA mutation-baring ES cells into mouse balstocysts. The resulting chmeric females were bred an a mouse lineage generated that was homoplasmic (pure mutant) for the mtDNA mutation and thus genetically stable. The introduction of the COI missense mutation into the mouse mtDNA resulted in a 50% reduction in tissue cytochrome c oxidase specific activity in all tissues. The COI mutant mice are born normal, but as they age they develop a progressive hypertrohic cardiomyopathy and myopathy. Moreover, tissue analysis has revealed the presence of hyerproliferative lesions, particularly in the urogenital track. Hence, we have created the first mouse harboring a stable mtDNA mutation that predisposes the animals to the premature onset of a variety of age-related diseases.

By creating such a mouse applicants have proven that mtDNA mutations are both necessary and sufficient to cause a variety of age-related diseases, thus demonstrating that a major drug target for treating age-related diseases should be the mitochondrion. Moreover, since these mouse have a predicable phenotypic progression, they becomes the perfect model of screening for presymptomatic preventative medications.

Prior to the present invention, there was a need in the art for a mammalian (mouse) model of mtDNA age-related degenerative diseases that would reproducibly generate a series of specific symptoms at defined stages in life. The present invention satisfies this need by providing such a mouse model. The mouse model of the present invention is useable to study and further define the the pathophysiology of mtDNA diseases and for the screening, development and testing of drugs, biologics and other therapies that may be effective in treating mtDNA age-related degenerative diseases.

Methods for introducing mtDNA mutations into the female mouse germline have been developed by Applicant's laboratory over the past 15 years. See, MacGregor, G. R., Fan, W. W., Waymire, K. G., and Wallace, D. C., *Generating Animal Models Of Human Mitochondrial Genetic Disease Using Mouse ES Cells* (2005) and Notarianni, E. and Evans M. J. (eds), *Embryonic Stem Cells*, Oxford University Press. pp 72-111. However, prior to the present invention, it remained unclear as to what type of mtDNA mutations could be introduced into the mouse female germline in a pure (homolasmic) state that would result in the stable transmission of the disease phenotype without killing the mice. Also, once such mice could be generated, it was unclear what would be the nature of the phenotype that would be generated and the timing of the development of the phenotype. All of these issues have been resolved by the present invention.

The present invention provides a mouse model that encompasses stably inherited homoplasmic mtDNA missense mutations that result in the predicable onset of a number of age-related degenerative disease and cancer phenotypes, only a subset of which have presently been fully characterized. Hence, the mouse model of the present invention will be of value in determining the pathophysiological role of the mitochondrion in age-related diseases and in the developing and screening of therapies (e.g., drugs, biologics, other therapies).

In accordance with the present invention, cells were grown in Dulbecco's modified Eagle's medium (DMEM) supplemented with 10% Hyclone fetal bovine serum (FBS). Mouse LA9 (HPRT$^-$) cells were cultured in 1 µg/ml Antimycin A (AntA) for 60 days and then cloned in 1 µg/ml AntA (NLAP clones). The mtDNA sequence of NLAP03 clones revealed that they were homoplasmic for a C insertion in the ND6 gene at np 13885. These cells also proved to be homoplasmic for a COI T6589C missense mutation (V421A, conservation index=100%). Both the ND6 13885insC {Bai Y & Attardi G, 1998, *EMBO J* 17:4848} and the COI T6589C {Actin-Perez R et al, 2003, *Hum Molec Genet* 12: 329} mutations have been isolated from LA9 cells previously, suggesting that they may have pre-existed within the LA9 cell line.

NLAP03 cells were enucleated by treatment with cytochalasin B and centrifugation through a Ficoll step gradient. The resulting cytoplasts were fused to LMEB4, a mtDNA-deficient ($\rho^\circ$) derivative of LM(TK$^-$), using polyethylene glycol. Cybrids were selected with 50 µg/ml bromodeoxyuridine in the absence of pyruvate and uridine. The resulting LMJL8 cybrids were also homoplasmic for the mtDNA COI T6589C and the ND5 13885insC mutations, and were used for further physiological and genetic studies.

MJL8 cells were again enucleated by Ficoll step gradient and the cytoplasts harvested, washed, and suspended in 0.3 M mannitol, pH 7.4. Mouse female ES cell line CC9.3.1 (HPRT) was cultured on mitomycin C-inactivated SNL76/7 feeder cells in DMEM+15% FBS+2 mM L-glutamine, 1× non-essential amino acids+100 µM β-mercaptoethanol. To remove the endogenous CC9.3.1 mitochondria, 2×10$^6$ CC9.3.1 cells were treated with 0.75 µg/ml rhodamine 6G (R6G) in the presence of 1 mM pyruvate and 50 µg/ml uridine for 72 hour. The R6G-treated CC9.3.1 cells were harvested, resuspended with the LMJL8 cytoplasts in 0.6 ml fusion medium, and the cells electrofused using a BTX ECM2001 pulse generator electro cell manipulator using an alignment of 20 sec AC at 50 volts followed by two 20 µsec pulses at DC 800V. After a 2 min recovery, the cells were plated on fresh feeder cells in medium containing HAT (hypoxanthine, aminopterin, and thymidine) to kill unenucleated LMJL8 cells and in the absence of uridine and pyruvate to block the growth of the R6G-treated CC9.3.1 cells. Only CC9.3.1 cells that were rescued by fusion with the LMJL8 cytoplast mitochondria were likely to grow and form colonies.

Ninety-six clones were isolated from the enucleated LMJL8×R6G-treated CC9.3.1 fusion, and the correct origin of their nuclei confirmed using micro-satellite polymorphisms at the D3Mit256, D8Mit289, and D10Mit10 loci. The proportion of the mtDNAs in each of the 96 clones that harbored the ND6 13885insC was then determined and 33 clones were found to be homoplasmic for the wild type ND6 sequence and 63 had varying percentages of the ND6 13885insC mutation. Three clones, EC53, EC95, and EC96 were homoplasmic for the ND6 13885insC, while clone EC77 was 96% ND6 13885insC and 4% ND6 13885insCdelT.

The EC77 cybrids with COI T6589C+ND6 13885insC and COI T6589C+ND6 13885insCdelT mtDNAs were injected into C57BL/6NHsd female blastocysts which were transferred into pseudopregnant females. Agouti-black female chimeras were identified and mated with C57BL6/J males. The mtDNA genotypes of agouti offspring and all subsequent crosses between the derived females and B6 males were determined from tail DNA, with the percentage of ND6 13885insC versus 13885insCdelT quantified by primer extension.

Heteroplasmic Mouse Model

A variety of procedures including ooplasmic injection to increase the fertility of eggs of older women (Barritt J A et al, 2001, Hum Reprod 16: 513-516) and nuclear transplantation to generate HLA matched human embryonic stem (ES) cells for cell replacement therapy (Dominko T, et al, 1999, Biol Reprod 60: 1496-1502; Yang C-X., et al., Molec Reprod Devel 65: 396-401) result in the mixing of mitochondrial DNAs (mtDNAs) of two different origins in the same cytoplasm. While both procedures are actively being considered for human use and ooplasmic transfer has already been used to generated heteroplasmic human babies, the pathophysiolgical significance of the mixing of two different mtDNAs has never been investigated.

There is increasing evidence that the accumulation of a diverse array of somatic mtDNA mutations is a critical factor in aging and age-related degenerative diseases {Trifunovic A et al, 2004, Nature 429: 417-423; Kujoth G C, et al, 2005, Science 309: 481-484; Schriner S., et al, 2005 Science 308 (5730)1909-1911}. For these reasons, it has become imperative that a heteroplasmic mouse model be developed and characterized to investigate the pathophysiological consequences of having a cytoplasm with two different mtDNAs and together associated divergent alleles. Not only will such a mouse model permit us to determine what adverse affects that can be expected in humans, it will provide us a platform to identify and evaluate therapeutic modalities that might help to ameliorate the daverse affects of the mtDNA heteroplasmy. To accomplish this goal, Applicants have created a mouse model in which mtDNAs from the NZB and 129 mouse strains were mixed in the same cytoplasm. These mtDNA differ at approximately 92 nucleotide positions.

Characterization of these heteroplasmic mice has revealed that they have an increased mtDNA somatic mutations rate, that their mtDNA undergo active recombination, that approximately ⅓ of the heteroplasmic mice die as neonates, that the surviving mice have a reduced life span, that the mice develop a diverse array of cancers, and that the animals develop a dramatic dilated cardiomyopathy within the first year of life. Therefore, these heteroplasmic mice demonstrate that simply combining a diverse array of mtDNA variants in the same cytoplasm is highly deleterious, provide the opportunity to determine why, and thus open the way for developing new therapeutic approaches to intervening in age-related degenerative diseases, cancer, and aging itself.

There have been two publications that have reported the generation of heteroplasmic mice. The first report was from my laboratory in which we described the creation of the NZB-129 heteroplasmic mice {Sligh, J. E., et al, 2000, Proc. Natl. Acad. Sci. USA 97:14461-14466}. However, we have not reported any phenotypic characterization of these mice. The second paper reported the introduction of a mtDNA deletion mutation into the mouse germline as a heteroplasmic mutation together with wild type mtDNAs {Inoue, K. et al., 2000, Nature Genetics 26: 176}. However, a mtDNA deletion merely creates a reduction in some of the polypeptides and tRNAs. This does create the dominant negative situation that can occur when two incompatible polypeptide alleles are used to assemble the same respiratory complex. This later condition is the one that Dr. Wallace has predicted will be highly deleterious and result in age-related degenerations {Wallace D. C., 2007, Ann Rev Biochem 76:781-821}. The current data provides the first direct evidence that simply mixing mtDNAs harboring two different but otherwise normal alleles is highly deleterious.

The problem was to develop a reliable mouse model in which two mtDNAs with a variety of different alleles could be routinely maintained in the mouse maternal germline on a uniform nuclear DNA background. These animals could then be reproducibly studied to determine their predisposition to age-related diseases, cancer and aging. Such a model would permit the definition of the pathophysiology of mtDNA disease and the development of disease and to evaluate of effective therapeutics.

Developing heteroplasmic mice has proven difficult for multiple reasons. First, there has been no reliable method for introducing mtDNA mutations into the female mouse germline. Over the past 15 years, Dr. Wallace's laboratory has now perfected such methods {MacGregor, G. R., Fan, W. W., Waymire, K. G., and Wallace, D. C., 2005, Generating animal models of human mitochondrial genetic disease using mouse ES cells. In Notarianni, E. and Evans M. J. (eds). *Embryonic Stem Cells*, Oxford University Press. pp 72-111}. Second, is has been unclear what type of mtDNA mutations could be introduced into the mouse female germline in the heteroplasmic state and would result in the stable transmission of the disease phenotype without killing the mice. Third, once such mice could be generated, it was unclear what would be the nature of the phenotype that would be generated and the timing of the development of the phenotype. All of these issues have been resolved with this current mouse model.

The heteroplasmic mouse model of the present invention encompasses a stably inherited set of about 92 heteroplasmic mtDNA base substitutions mutations which cause a predicable onset of a number of age-related degenerative disease and cancer phenotypes. Hence, this model will be of enormous value in determining the pathophysiological role of the mitochondrion in age-related diseases and in the developing and screening of preventative therapeutics.

To combine the NZB and 129 mtDNA in the same mouse cytoplasm, we first needed to identify a female mouse embryonic stem (ES) cell line that would go germline and make oocytes. This led to our development of the CC9.3.1. CC9.3.1 cells are of 129 origin and thus contained 129 mtDNA, which is of the "common haplotype" mtDNA. By contrast, NZB mice were derived from Swiss mice and their mtDNAs differ from this "common haplotype" by 92 nucleotide substitutions, one of which creates a BamHI restriction site polymorphism.

To mix the 129 mtDNAs with NZB mtDNAs, we first needed to recover the NZB mtDNAs from NZB mice. To accomplish this, we took advantage of the fact that if brains are gently homogenized, the synaptic botons which are rich in mitochondria break off and can be isolated in Percoll gradients. These mitochondria-containing synaptosomes from NZB mouse brains were isolated and fused to our mouse LMEB4 cell line which lacks its own mtDNA ($\rho^\circ$). Cybrids having the nuclear DNA of the LM(TK$^-$) cells, but the NZB mtDNAs were selected in the absence of uridine and in the presence of BrdU. The resulting LMEB4(mtNZB) cybrids were then enucleated and the cytoplasts fused to CC9.3.1 cells that had been treated with the mitochondrial toxin, rhodamine 6G (R6G), to reduce the level of resident 129 mtDNAs.

The resulting CC9.3.1(mtNZB) cybrids were injected into C57B16/J (B6) embryos and mice with a high degree of chimerism generated. One female chimeric mouse, heteroplasmic for the NZB and the "common haplotype" mtDNAs, was matted with two different B6 males and the heteroplasmic mtDNAs were transferred to all of the seven and ten offspring, respectively. A female of the next generation was matted to a B6 male and transmitted the heteroplasmic mtDNAs to her seven progeny, while a heteroplasmic male mated to two B6 females did not transmit the NZB mtDNAs to any of his sixteen offspring. Hence, this experiment established that the heteroplasmic mtDNAs could be transmitted through the female mouse germline {Sligh, J. E., et al, 2000, *Proc. Natl. Acad. Sci. USA* 97:14461-14466}. Over the past seven years, these heteroplasmic females have been repeatedly backcrossed to B6 males, which has continued through over 15 generations. Hence, all of the mice now have an identical nuclear genetic background.

At genetation 12, a portion of the animals were permitted to randomly segregated their mtDNAs. This resulted in one lineage that reverted back to pure 129 mtDNAs. All subsequently experiments have compared the heteroplasmic with the homoplasmic mice. The heteroplasmic mice have been found to be strikingly physically impaired.

EXAMPLE 1

Homoplasmic COI T6589C Missense Mutant Mouse Model for Hypertrophic Cardiomyopathy Hypertrophic cardiomyopathy in humans has been linked to mutations in 11 sarcomeric protein genes. Recessive null mutants in the human heart-muscle ANT isoform gene (ANT1) have also been reported to cause hypertrophic cardiomyopathy. Some hypertrophic cardiomyopathy patients have been identified with both sarcomeric protein and mtDNA mutations, and hypertrophic cardiomyopathy has been associated with mtDNA mutations alone. Thus, hypertrophic cardiomyopathy appears to be the common adaptive strategy for both reduced contractile force and reduced mitochondrial energy production.

Mouse models of hypertrophic cardiomyopathy have been heretofore been generated by introduction of certain of the human pathogenic mutations into the mouse sarcomeric protein genes. Hypertrophic cardiomyopathy has also been also heretofore been induced in Ant1 null mice.

In this example, Applicants describe the creation of a new mouse model for inherited hypertrophic cardiomyopathy by the introduction of a mutant mtDNA into a mouse germline. Specifically, a female mouse was created whose mtDNA was homoplasmic for a COI missense mutation (T6589C) and 50-50 heteroplasmic for an ND6 C insertion frameshift mutation (13885insC) and a T deletion reversion of that mutation (13885insCdelT). This mouse was backcrossed to C57BL/6J males, which led to the directional loss of the frameshift mutant mtDNA within four generations. The resulting homoplasmic COI T6589C missense mutant mouse had a 50% reduction in complex IV activity and developed a severe hypertrophic cardiomyopathy with abnormal mitochondria. Thus, severe mtDNA mutations can be selected against in the female germline and inherited cardiomyopathy can be caused by a mtDNA mutation.

Maternally inherited mitochondrial DNA (mtDNA) has a high mutation rate and mtDNA base substitution mutations have been linked with a wide range of inherited human degenerative diseases including cardiomyopathy, myopathy, neurological manifestations, and endocrine disorders. Analysis of the mechanism of transmission of deleterious mtDNA base substitution mutations and their mammalian pathophysiology can be facilitated by use of mouse models. Mouse lines have been produced in which an inherited mtDNA deletion is associated with myopathy and a mtDNA 16S rRNA mutation with dilated cardiomyopathy. However, to date, no mouse line has been reported harboring a mtDNA missense mutation that results in a maternally-inherited disease phenotype.

The segregation of deleterious heteroplasmic mtDNA mutations in human families has been studied extensively, but the relative importance within the female germline of genetic drift versus selection remains unknown (6). Mice heteroplasmic for two "normal" mtDNAs show random segregation by genetic drift, but the rarity of maternal transmission of very severe mtDNA mutations suggests that selection may also play and important role.

Figure 1A:
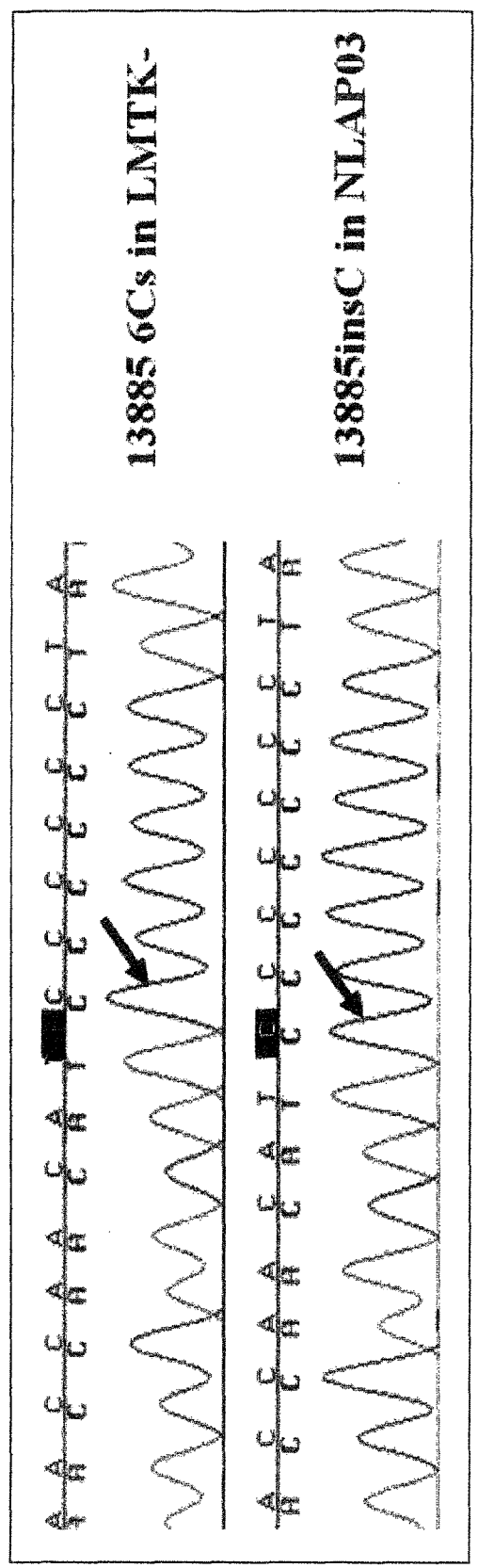
Figure 1B:
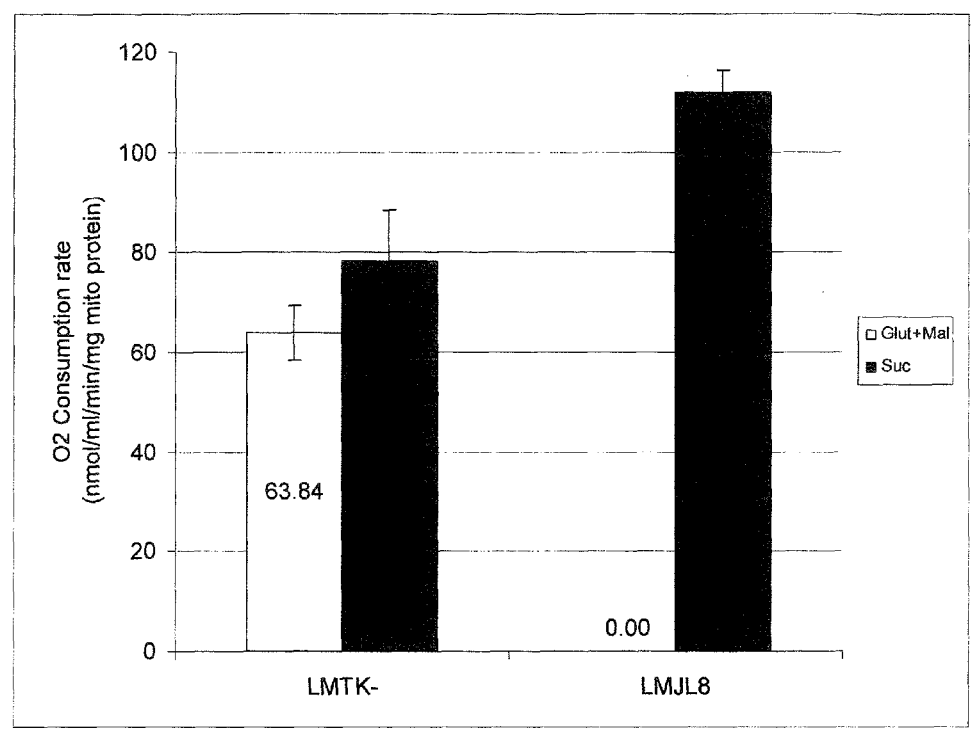

To establish mouse models of mitochondrial disease resulting from mild and severe polypeptide mutations, we isolated a mouse LA9 cell line resistant to the respiratory inhibitor Antimycin A. This cell line, NLAP03, was homoplasmic for a frameshift mutation in ND6 caused by the insertion of a C at nt 13885 (ND6 13885insC). This mtDNA frameshift mutation was linked to a homoplasmic COI T6589C missense mutation (V421A) (FIG. 1A, B). The 13885insC mutation alters the ND6 reading frame at amino acid 63, with the out-of-frame amino acid chain ending at position 79. Comparable ND6 frameshift (9) and COI missense (5, 10) mutations have been reported to result in severe complex I and partial (≈50%) complex IV defects, respectively.

Figure 1C:
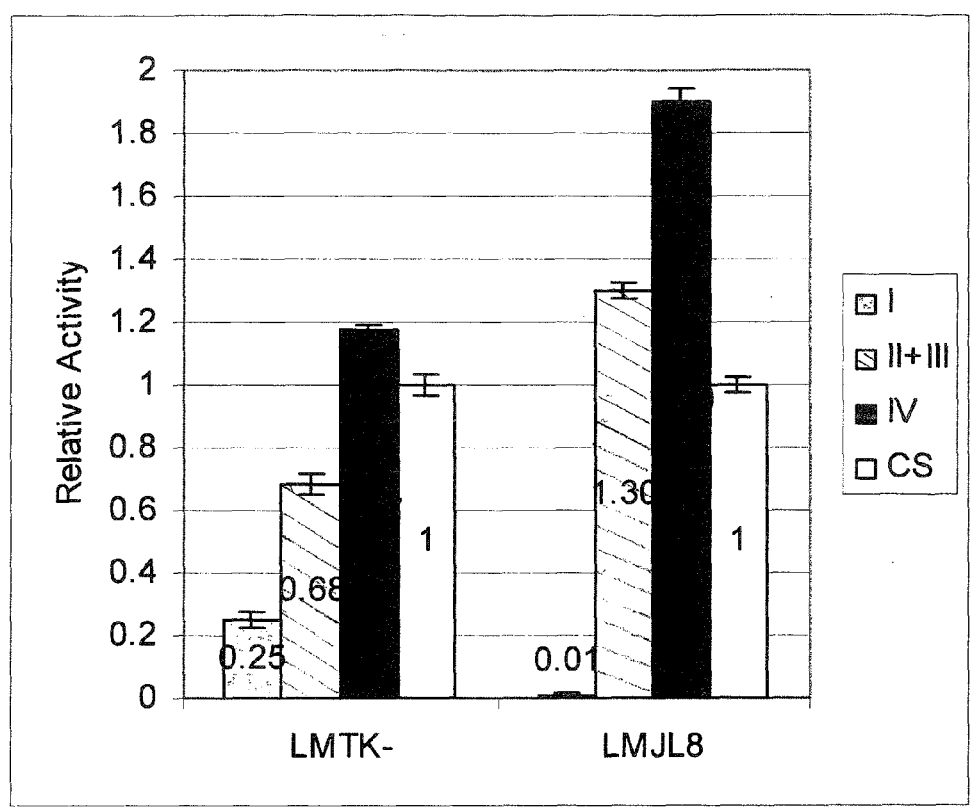
Figure 1D:
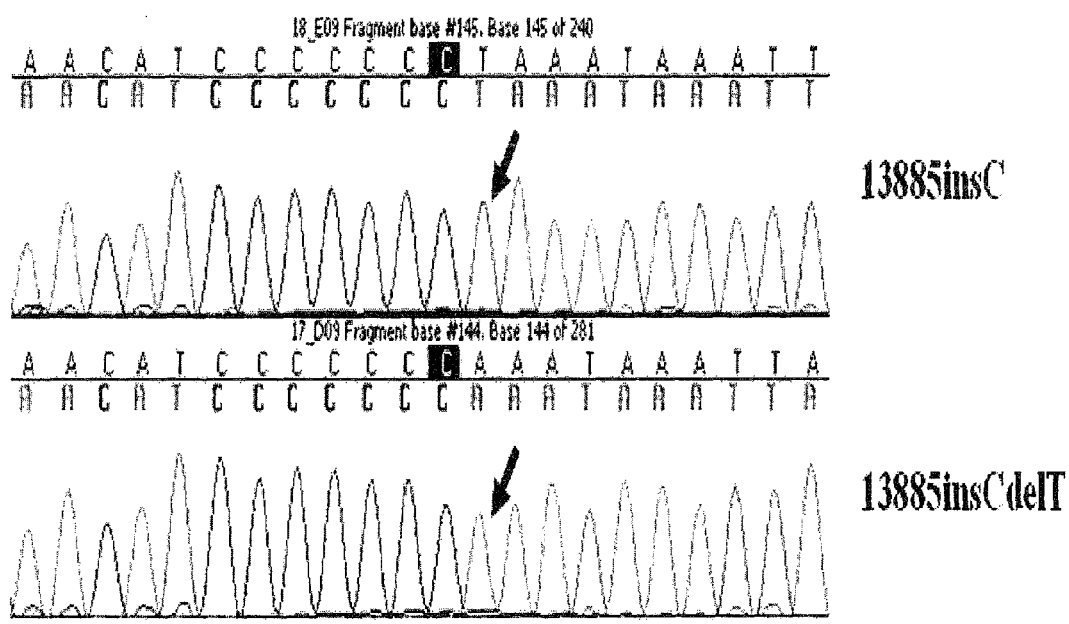

To facilitate biochemical and genetic analysis, the NLAP03 double mutant cell line was enucleated and the mtDNA-containing cytoplasts fused to our mtDNA-deficient ($\rho^\circ$) LM(TK$^-$) cell line LMEB4. Cybrids were selected in medium containing bromodeoxyuridine (BrdU) but lacking uridine and pyruvate (11). The resulting LMJL8 cybrid was homoplasmic for the ND6 13885insC+COI T6589C mtDNA. Relative to LM(TK$^-$), the LMJL8 mitochondria (11) had no NADH-linked respiration and no detectable complex I enzyme activity, a 43% increase in succinate-linked respiration, a 91% increase in complex II+III activity, and a 62% increased in complex IV activity (FIG. 1C, D). The increased complex II and III activities suggest that LMJL8 cells can compensate for the complex I defect by increasing activity of the other oxidative phosphorylation (OXPHOS) complexes. We previously observed increased complex IV activity in adenine nucleotide translocator (ANT) deficient mice. Thus the compensatory induction of complex IV in response to the complex I defect masks the expected reduction in complex IV activity caused by the COI T6589C mutation.

Figure 1E:
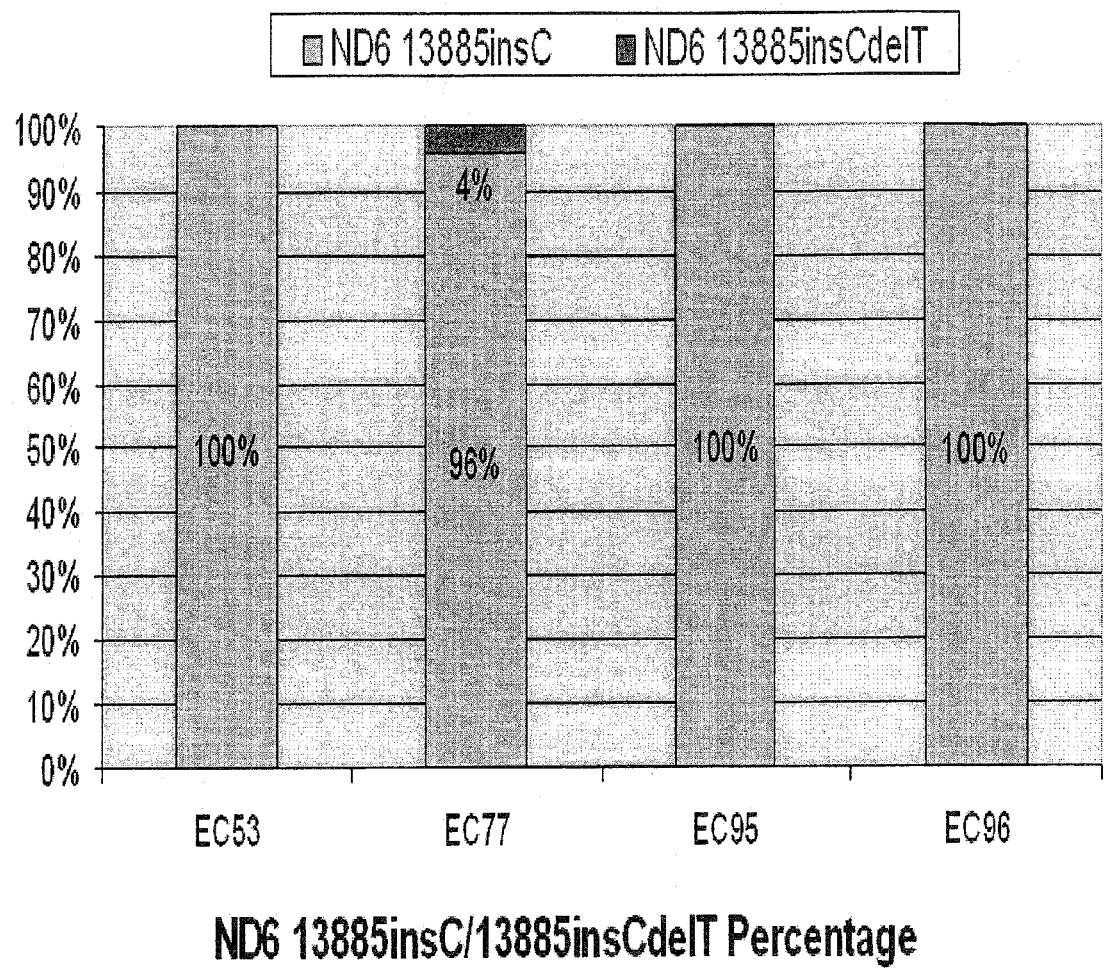

LMJL8 cells were enucleated and the cytoplasts containing the ND6 13885insC+COI T6589C mutant mtDNAs were fused to CC9.3.1 (origin) 129SvEv-Gpi1$^c$) female ES cell line which had been cured of its resident mtDNAs by treatment with the mitochondrial toxin rhodamine 6G. Ninety six ES cybrids were isolated and screened by a primer extension assay (Fig. S1). Four cybrids (EC53, EC77, EC95, and EC96) were further characterized by cloning the 13885 mutant region from multiple mtDNAs and sequencing the insertion site. All four cybrids were homoplasmic for the COI T6589C mutation and three were homoplasmic for the ND6 13885insC frameshift mutation. However, one cybrid, EC77, was found to have mtDNAs, 96% of which had the ND6 13885insC frameshift mutation but 4% had an additional reversion mutation in which the T adjacent to the ND6 13885insC was deleted (13885insCdelT). This reversion was remarkable in that it restored the normal ND6 amino acid sequence, while converting the leucine codon 60 from TTA to TTG (FIG. 1E, F).

Figure 2:
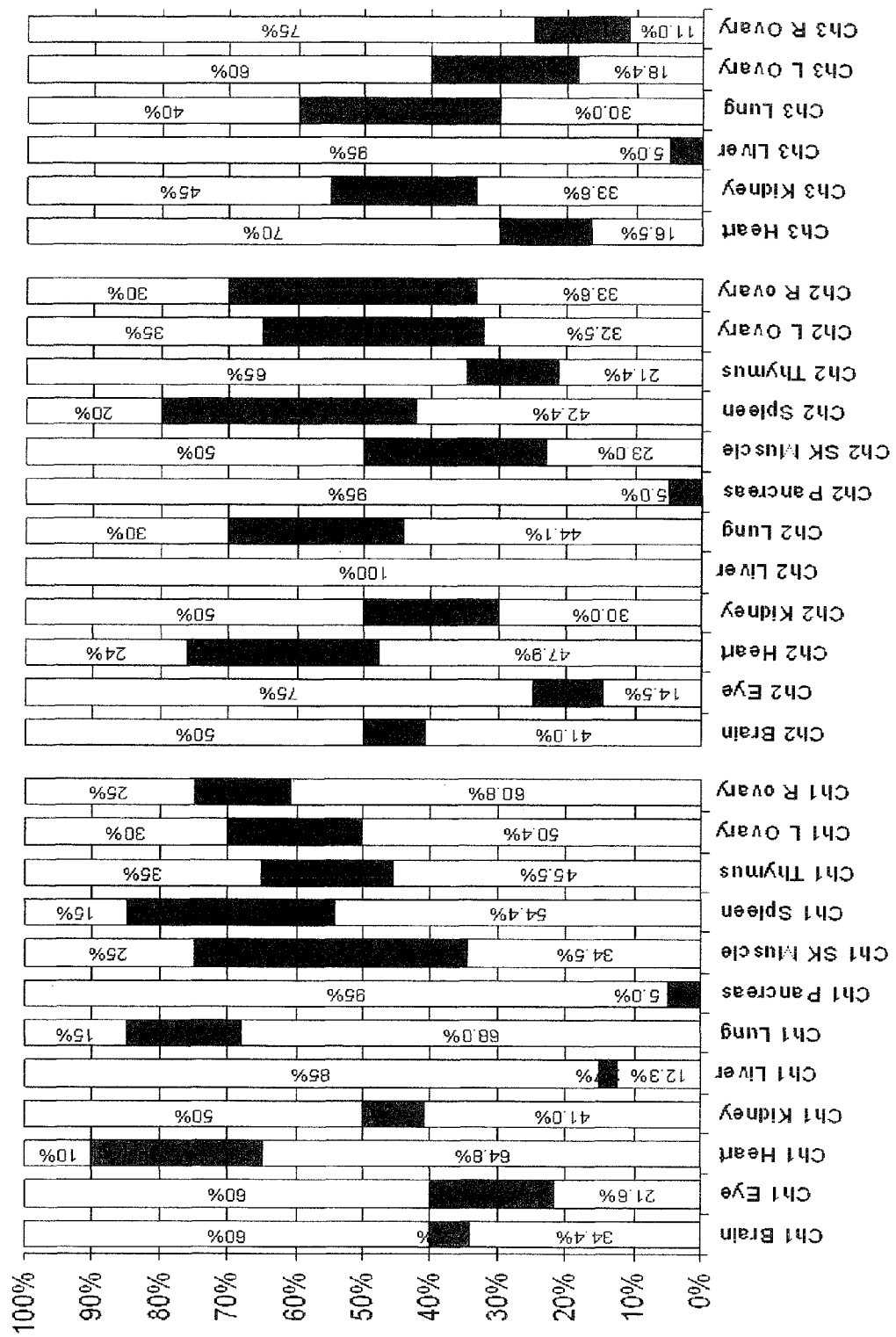
FIGS. 2A-2B show the proportion of ND6 wild type, 13885insC frameshift, and 13885insCdelT revertant mtDNAs in tissues of chimeras CH1, CH2, and CH3 and tails of EC77-AG and its offspring as described in Example 1 below. Specifically.
Figure 2A:
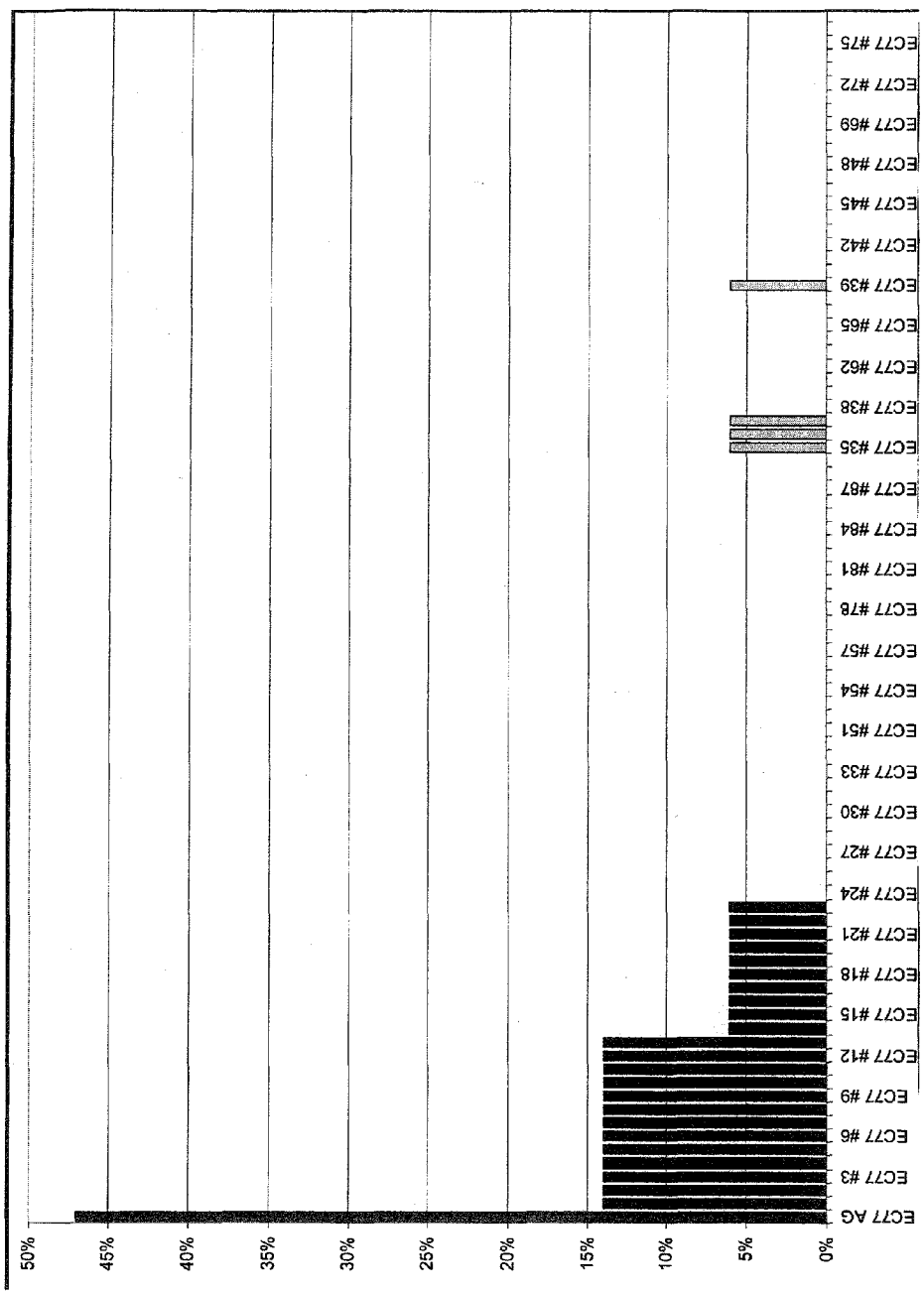

EC77 cells were then injected into female C57BL/6NHsd blastocysts, and the chimeric embryos transferred into pseudo-pregnant females. Three chimeric females were obtained (designated CH1, CH2, and CH3) with estimated levels of chimerism based on agouti coat color of 80-90%, 50-60%, and 30-40%, respectively. Following breeding, the three chimeric females were euthanized at age 14 months and various tissues genotyped for the ND6 mutations. Most tissues from the chimeric females contained variable amounts of three types of mtDNA: wild type mtDNA from the B6 blastocyst cells, ND6 13885insC frameshift+COI T6589C mtDNA, and ND6 13885insCdelT reversion+COI T6589C mtDNA, the later two from the EC77 cells (FIG. 2A). As anticipated, the average percentage of mutant mtDNA in different tissues in each of the three mice was directly related to the estimate of chimerism based on coat color (CH1, 58%; CH2, 48%; CH3, 35%). However, the ratio of the 13885insC frameshift to 13885insCdelT revertant mtDNA had declined from 96% in the original ES77 cell line to 63±13% in different tissues of the three chimeric mice. Indeed, in the liver and pancreas of two of the three animals the 13885insC frameshift mtDNA was undetectable. Hence, selection against the 13885insC frameshift mutation had already occurred during development of the chimeras.

Figure 3:
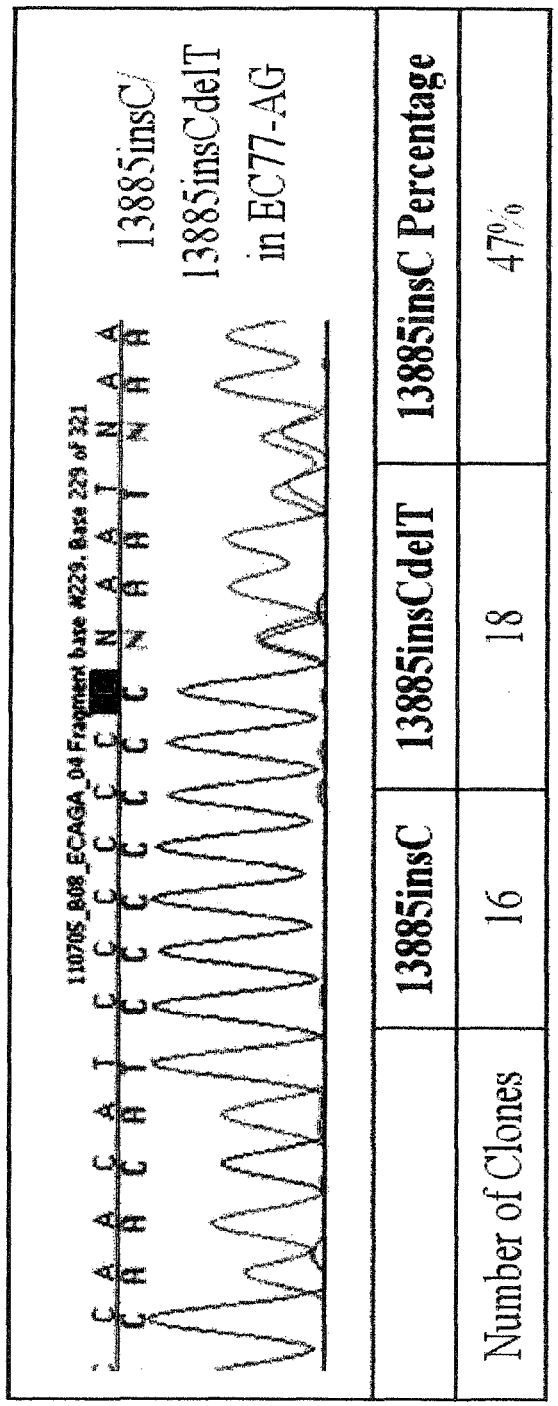
FIGS. 3A-3E show analysis of the mtDNAs and mitochondria of the EC77-AG founder tissues and the mtDNAs in 12 individual oocytes from 14% ND6 13885insC females as described in Example 1 below. Specifically.
Figure 3A:
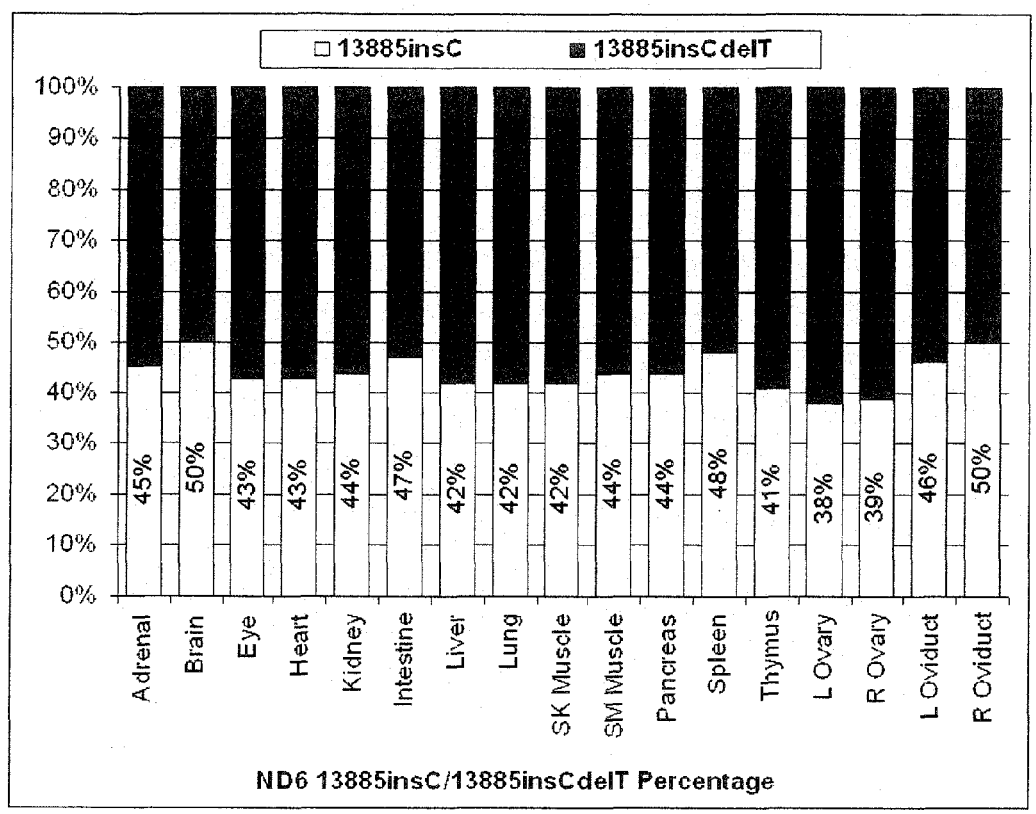
Figure 3B:
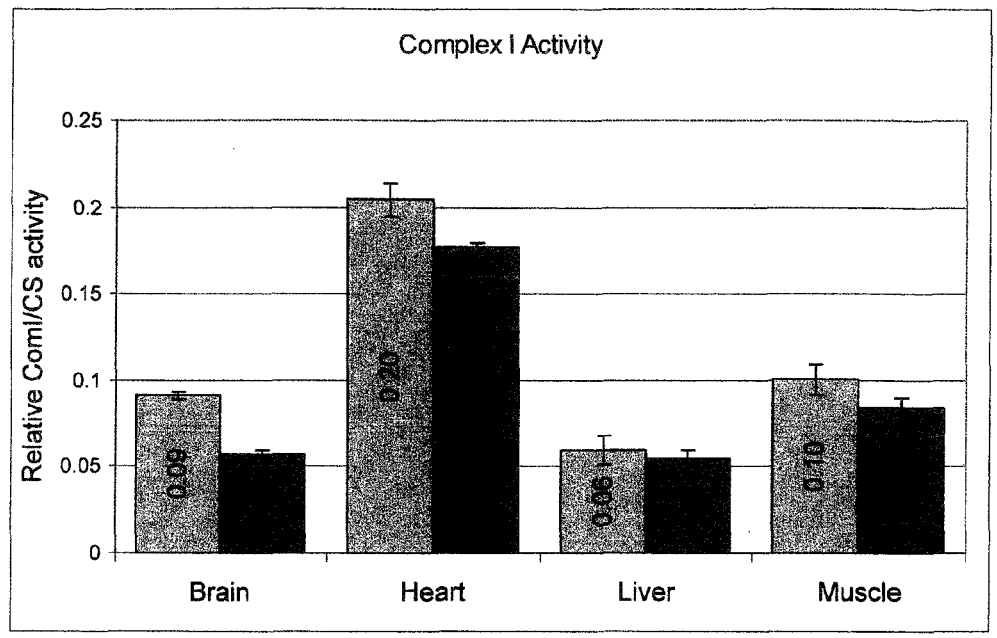

The CH1, CH2, and CH3 chimeric females were mated with C57BL/6J (B6) males starting at age two months and produced a total of 42, 33, and 36 pups, respectively. Only one of the 111 pups, EC77-AG from chimeric mother CH3, was agouti and therefore ES-cell derived. This animal was female and able to transmit her mutant mtDNAs to her offspring (FIG. 2B). The tail mtDNA of female EC77-AG was homoplasmic for the COI mutant allele, but heteroplasmic for the ND6 frameshift and revertant alleles (100% COI T6589C, 47% ND6 13885insC frameshift and 53% ND6 13885insCdelT revertant), determined by both primer extension and cloning and sequencing (FIG. 3A). In contrast to her mother (CH3), when analyzed at age 11 months, EC77-AG's tissues were relatively uniform in the proportion of the ND6 13885insC frameshift and ND6 13885insCdelT revertant mtDNAs, with an average of 44±3% (range 38% to 50%) ND6 13885insC frameshift mtDNAs. The highest level of the frameshift mutant mtDNA was found in the brain, the lowest in the ovary (FIG. 3B).

Figure 3C:
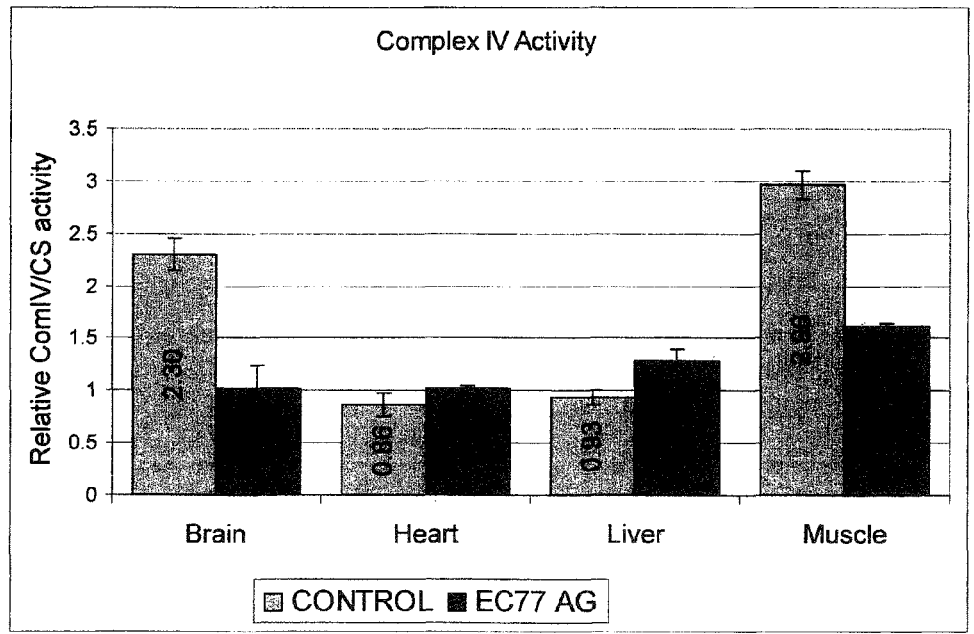
Figure 3D:
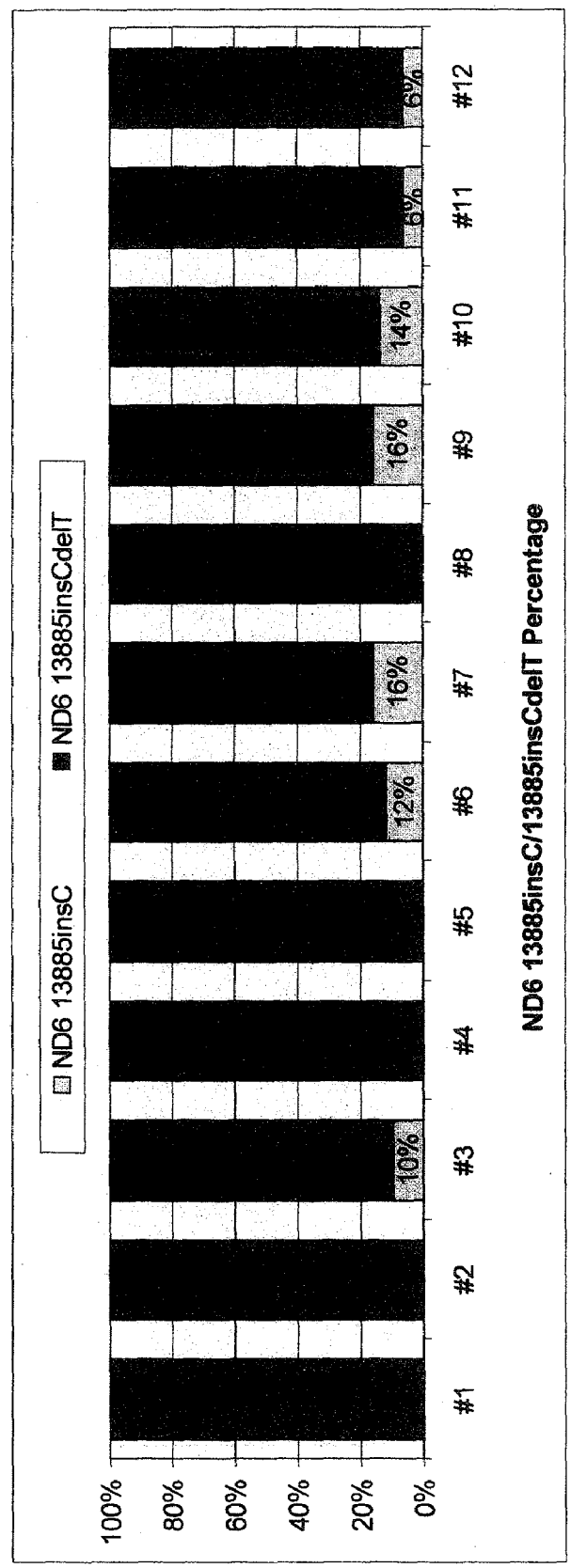
Figure 4:
FIGS. 4A-4I show transmission electron micrographs of skeletal muscle and hearts from B6 control mice and EC77 mutant mice harboring 0%, 14%, and 47% ND6 13885insC frameshift and 100% COI T6589C missense mtDNAs as described in Example 1 below. Specifically.
Figure 4A:
Figure 4B:
Figure 4C:
Figure 4D:
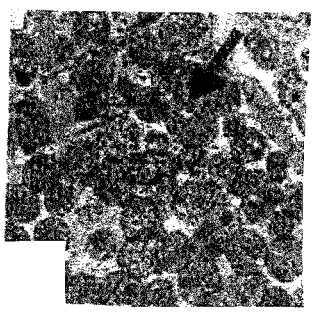

Throughout 11 months of life EC77-AG displayed no overt phenotype. However, ultrastructural analysis at necropsy revealed that the heart mitochondria of the mutant were associated with what appear to be lipid droplets [FIG. 4A (control) versus FIG. 4C (mutant)] while the muscle mitochondria showed abnormalities and degeneration [FIG. 4B (control) versus D (mutant)]. Mitochondrial enzymatic assays revealed a 10% to 33% decrease of complex I activity in brain, heart, liver and skeletal muscle (FIG. 3C), a 56% and 46% decrease of complex IV activity in brain and skeletal muscle, and a 19% and 39% increase of complex IV activity in its heart and liver (FIG. 3D). Again, the variability in complex IV activity was interpreted as an effect of the COI missense mutation causing increased complex IV activity.

Female EC77-AG (F1) was mated with B6 males and gave birth to 6 litters totaling 56 pups (N2). Primer extension analysis of the ND6 13885insC frameshift and 13885insCdelT reversion mutations revealed that the first litter of 4 pups (EC77 #1 to #4) and the second litter of 9 pups (EC77 #5 to #13) all had 14% of the ND6 13885insC frameshift mutation and 86% of the ND6 13885insCdelT reversion (FIG. 2B). The third litter of 10 pups (EC77 #14 to #23) all had 6% of the ND6 13885insC frameshift mutation and 94% of the ND6 13885insCdelT reversion. The fourth litter of 11 pups (EC77 #24 to #34), the fifth litter of 10 pups (EC77 #50 to #59), and the sixth litter of 12 pups (EC77 #78 to #89) had all lost the frameshift mtDNA (0% of the ND6 13885insC and 100% ND6 13885insCdelT) (FIG. 2B).

N2 female EC77 #4 with 14% ND6 13885insC frameshift mtDNAs was mated with B6 males and had 2 litters totaling 12 pups (N3) (FIG. 2B). Three of the 4 pups of the first litter had 6% ND6 13885insC frameshift and 94% ND6 13885insCdelT reversion mtDNAs. The remaining pup of the first litter and all 8 pups of the second litter had completely lost the frameshift mtDNA (0% ND6 13885insC and 100% N13885insCdelT). N2 female EC77 #11 with 14% ND6 13885insC frameshift mutant mtDNA was also mated with B6 males and had 2 litters totaling 21 pups. One of the 11 pups of the first litter had 6% ND6 13885insC frameshift mutation and 94% ND6 13885insCdelT reversion mtDNAs. The remaining 10 pups of the first litter and all 10 pups of the second litter had lost the frameshift mtDNA (0% ND6 13885insC and 100% 13885insCdelT). Two N3 females with 6% ND6 13885insC frameshift mtDNAs were also mated with B6 males, but all 35 pups (N4) had lost the frameshift mtDNA (0% ND6 13885insC and 100% 13885insCdelT). Therefore, the ND6 13885insC frameshift mutation was directionally eliminated from the mouse female germline within 4 generations. Hence, mtDNAs harboring a highly deleterious frameshift mutation can undergo directional segregation suggesting that selection must be acting against severely deleterious mtDNA mutations in the female germline.

Figure 4E:
Figure 4F:
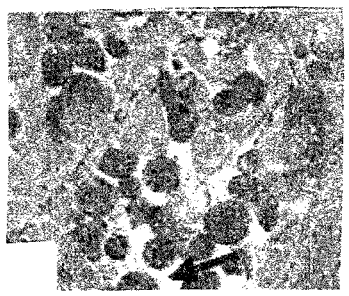
Figure 4G:

The tissue distribution of the ND6 13885insC frameshift mutation was analyzed in three N2 mice containing 14% ND6 13885insC and 100% COI T6589C mutant mtDNA. Again, the percentage of the ND6 13885insC frameshift mutant and 13885insCdelT reversion mtDNAs remained constant across tissues, the ND6 13885insC frameshift mutant mtDNA varying between 14% to 16% (Fig. S2A). Ultrastructure analysis of the hearts of the 100% COI T6589C+14% ND6 13885insC mutant mice revealed mitochondrial proliferation, evidence of mitochondrial autophagy, and myofibrillar degeneration (FIG. 4E-G). Biochemical analysis revealed no reduction in the complex I activities in brain, heart or liver, but a 28%, 70%, and 59% decrease of complex IV activities, respectively (Fig. S2B). Presumably, the 14-16% of ND6 13885insC frameshift mtDNAs was sufficient to induce a compensatory increase of complex IV activity. Consequently, the biochemical consequences of the COI T6589C mutation became manifest.

To determine if the directional loss of the ND6 13885insC frameshift mtDNA could occur during germline development, we collected individual oocytes from superovulated N2 females containing 14% of the ND6 13885insC frameshift mtDNA and determined the percentage of mutant mtDNAs in each oocyte by PCR amplification and primer extension. The ND6 13885insC region was successfully amplified from 12 of 16 oocytes, and the percentage of the ND6 13885insC frameshift mtDNA determined by primer extension. Five oocytes were found to have lost the frameshift mtDNA (0% ND6 13885insC and 100% ND6 13885insCdelT). Two oocytes retained 6% of the frameshift mtDNA (6% ND6 13885insC and 94% % ND6 13885insCdelT). The remaining 4 oocytes retained 10-16% frameshift mtDNA (10-16% ND6 13885insC and 84-90% ND6 13885insCdelT) (FIG. 3E). Hence, none of the oocytes contained more frameshift mtDNA than the female, and almost half had lost all of the ND6 13885insC frameshift mtDNA. Hence, the directional loss of the frameshift mutant mtDNAs must have occurred pre-ovulation.

Figure 5:
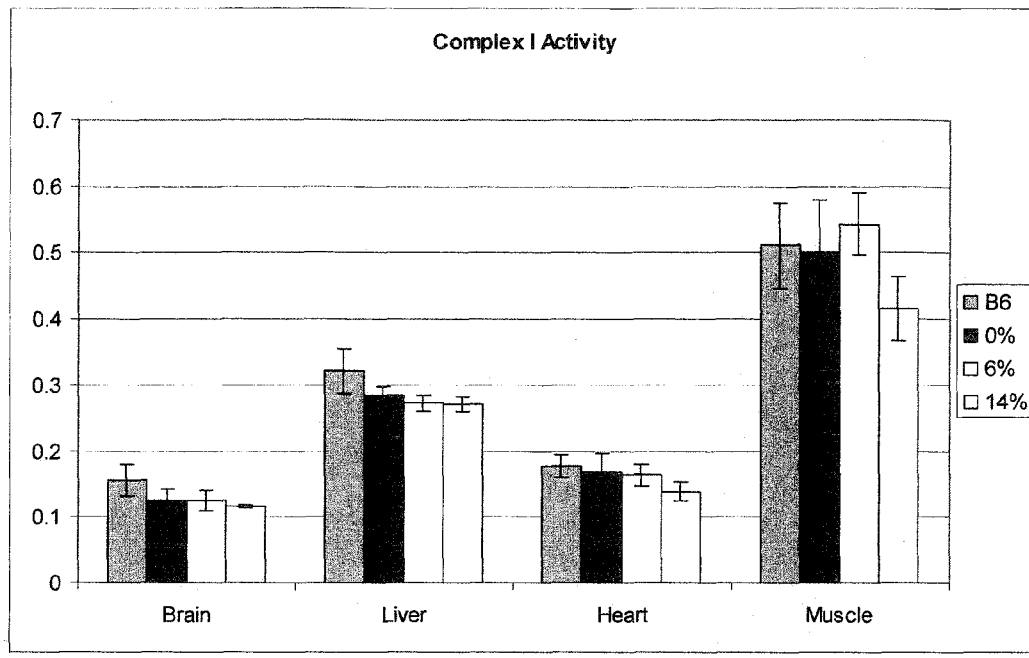
FIGS. 5A-5C show OXPHOS enzyme levels in mice harboring 0%, 6%, or 14% ND6 13885insC frameshift and 100% COI T6589C missense mtDNAs as described in Example 1 below. Specifically.
Figure 5A:
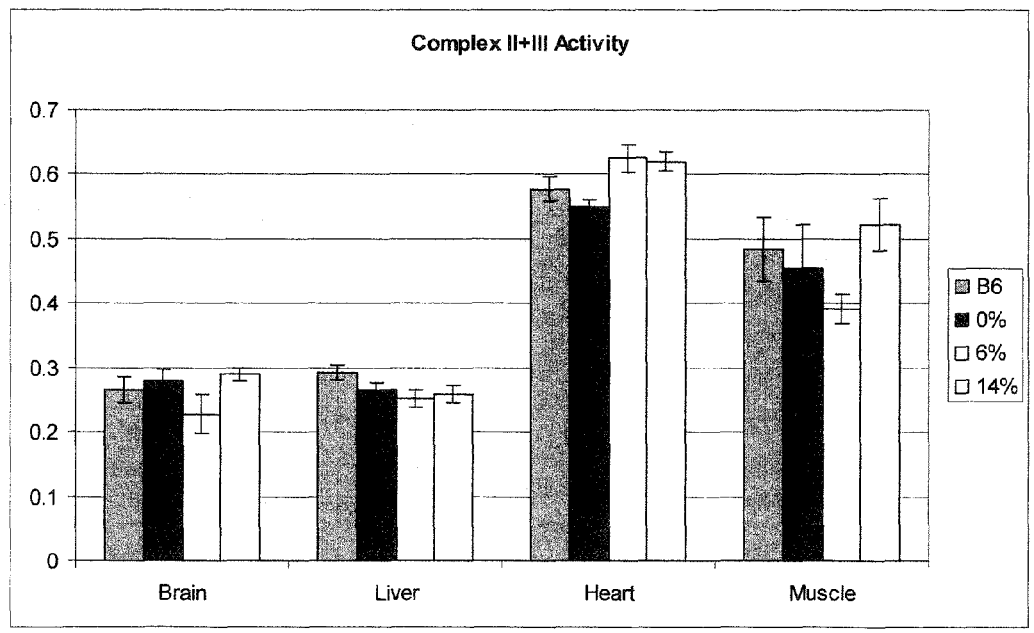
Figure 5B:
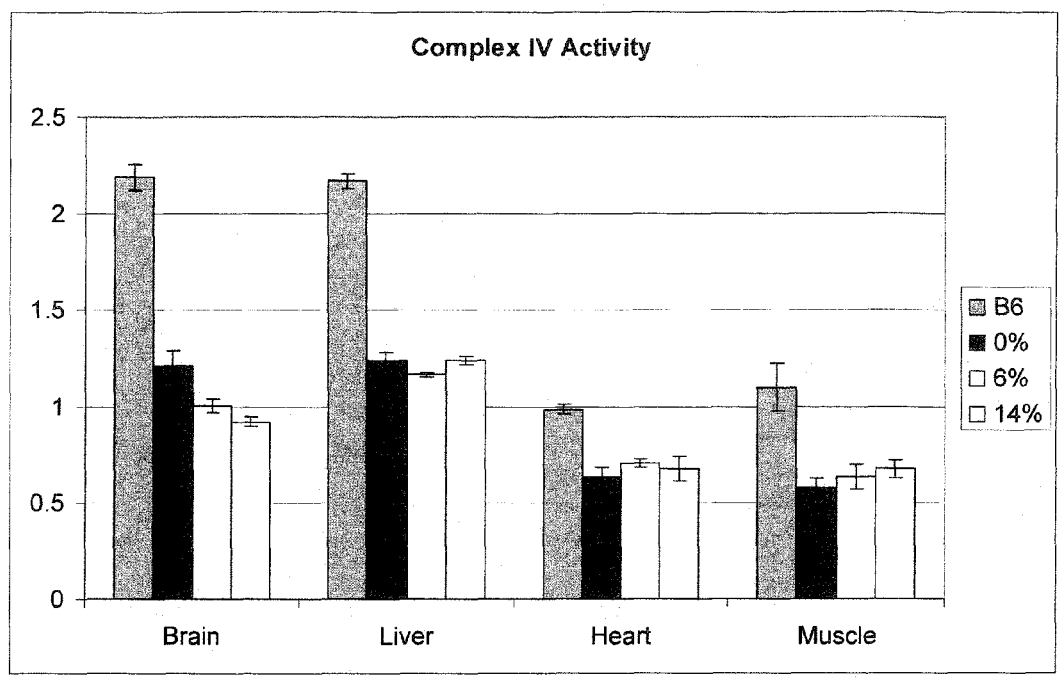

Next, we analyzed mitochondrial OXPHOS enzyme activity in brain, liver, heart and muscle of mice with 0%, 6%, or 14% ND6 13885insC frameshift mtDNA. Relative to B6 control mitochondria, no significant difference was seen in complex I activity in brain, liver, and heart. Similarly, there was no difference in complex I activity in muscle between B6 and 0 or 6% ND6 13885insC frameshift mutant mtDNAs, though there may have been a slight reduction in the complex I activity of the 14% ND6 13885insC frameshift mutant muscle (FIG. 5A). Also, no significant difference was observed in complex II+III activity for mice with these genotypes (FIG. 5B). In contrast, the complex IV specific activity for all of the mice was reduced approximately 50% in brain, liver, and muscle and about 30% in heart (FIG. 5C). Hence, the predominant biochemical defect in all of these genotypes could be attributed to the COI T6589C missense mutation.

Female mice homoplasmic for mtDNA with the COI T6589C missense, linked to the ND6 13885insCdelT revertant mutation, transmitted this mtDNA to all of their offspring, through multiple backcrosses to B6 males. While these mice appear grossly phenotypically normal, echocardiographic analysis of the mice at 12 months of age revealed that 100% of animals (n=7) had developed a striking hypertrophic cardiomyopathy, relative to age-matched B6 controls (n=5). The hypertrophic cardiomyopathy was associated with a 35% increase in left ventricular wall thickness (LVWT), a 23% reduction in left ventricular inner dimension at end-diastole (LVIDd) (P<0.001) and a 27% increase in rotation in association with a 28% reduction in circumferential strain vectors (P<0.001) and a 42% reduction in the radial stretch vectors (P<0.001) (FIG. 6). Hence, inheritance of the mtDNA COI T6589C missense mutation caused hypertrophic cardiomyopathy.

Figure 4H:
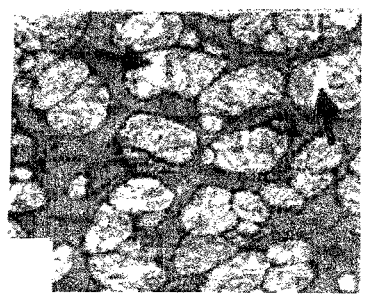

Cardiac dysfunction of COI T6589C mice was also associated with ultrastructural abnormalities including cardiac mitochondrial abnormalities. These included mitochondrial proliferation, reduction in mitochondrial matrix density and cristolysis, and loss of myofilaments (FIG. 4H, I). While the introduction of the mtDNA COI T6589C mutation into C57BL/6J mice resulted in a hypertrophic cardiomyopathy that was not seen in age-matched C57BL/6J mice without the mtDNA COI missense mutation, it is possible that C57BL/6J mice may be more prone to mitochondrial disease than other strains due to its lack of the nicotinamide nucleotide transhydrogenase (Nnt) gene. Irrespective of the status of the Nnt gene defect, our results prove that the introduction of the mtDNA COI T6589C (V421A) mutation into C57BL/6J mice causes hypertrophic cardiomyopathy.

Our observation of unidirectional loss of the ND6 frameshift mutant mtDNA (13885insC) from mice that started with nearly an equal proportion of frameshift and revertant (13885insCdelT) molecules stands in stark contrast to the apparently random segregation of mtDNAs that was observed when NZB and Balb/c mtDNAs were mixed together in the same mouse female germline. While the exact mechanism by which the ND6 frameshift mutant mtDNAs were eliminated is currently unknown, based on previous studies this may occur during oogenesis. Because primordial germ cells have a limited number of mtDNAs, it has been hypothesized that heteroplasmic female mtDNAs undergo rapid genetic drift during the approximately 20 cell divisions of the primordial germ cells that generate the oogonia within fetal ovigerous cords. This would result in a distribution of mtDNA genotypes arrayed around the maternal percent heteroplasmy. At around birth in rodents, the oogonia within ovigerous cords reorganize to form single oogonia surrounded by granulosa cells, with loss of a proportion of oogonia via apoptosis. In addition, in adult female mice, rats and humans, only around 30% of oocytes complete meiotic maturation with the remainder undergoing apoptosis. Defects in OXPHOS complex I are frequently associated with increased production of mitochondrial reactive oxygen species (ROS) and increased oxidative stress can induce apoptosis in pre-ovulatory follicles.

Based on these observations, we hypothesize that prior to reorganization of ovigerous cords in the newborn mouse, there was an array of oogonia with wide distribution of ratios of the ND6 13885insC frameshift and ND6 13885insCdelT revertant mtDNAs, with their mode corresponding to the maternal genotype. At some point between reorganization of the ovigerous cords and ovulation of mature follicles in the adult mouse, those oocytes with the highest proportion of the frameshift mtDNAs generated the most ROS and had the highest probability of undergoing apoptosis. Consequently, only the follicles with lower percentages of frameshift mtDNAs survived to be ovulated. Such a mechanism would result in the exponential loss of the deleterious mtDNA over successive generations, as observed. This model predicts that the greatest initial drop in percentage of frameshift mtDNAs would occur in the offspring of the founder female with a 50-50 ratio of frameshift to revertant mtDNAs, since she would have generated the greatest distribution of pre-oocyte genotypes. Subsequent mothers with lower percentages of frameshift mtDNAs would generate oogonia or oocytes with mtDNA genotypes biased toward a predominance of revertant mtDNAs. Consequently, their surviving ovulated oocytes would have a mtDNA frameshift to revertant ratio that was less than or equal to that of their mothers.

Regardless of the actual mechanism, we were ultimately left with mice that were homoplasmic for the COI T6589C missense mutation on a mtDNA background that contained the 13885insCdelT reversion ND6 gene. These animals now breed true for this mtDNA genotype, which results in hypertrophic cardiomyopathy by middle age in association with mitochondrial structural anomalies. This phenotype is unlikely to arise from inheritance of a nuclear DNA mutation as the phenotype is retained despite several generations of transfer of the mutant mtDNA into mice with a wild type nuclear background. Hence, mitochondrial energy deficiency resulting from a mtDNA missense mutation is sufficient to generate hypertrophic cardiomyopathy.

Applicants' demonstration that hypertrophic cardiomyopathy can be caused by either nDNA or mtDNA mutations in mitochondrial OXPHOS genes broadens our understanding of the pathophysiology of human hypertrophic cardiomyopathy and adds a new dimension to the molecular diagnosis of these patients. Moreover, the mitochondrial etiology of certain forms of hypertrophic cardiomyopathy suggest novel strategies for both the genetic and metabolic treatment of these life threatening conditions.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element, attribute, component or step of one embodiment or example may be incorporated into or used with any other embodiment or example, unless to do so would render that embodiment or example unsuitable for its intended use. Also, where the steps of a method or process are described, listed or claimed in a particular order, such steps may be performed in any other order or in combination(s), unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A a mouse whose mitochondrial DNA (mtDNA) comprises engineered mutations, wherein said mutations comprise:
   (a) a homoplasmic COI T6589C missense mutation and,
   (b) a T deletion reversion of a 1388insC mutation (1388inscCdelT) in the ND6 gene, wherein said mouse has mtDNA from mouse strains NZB and 129 mixed in the same cytoplasm; and
   wherein said mouse exhibits hypertrophic cardiomyopathy and mitochondrial abnormalities.

2. A mouse according to claim 1 wherein said mouse is 50-50 heteroplasmic for an ND6 13885insC frameshift mutation and an ND6 13885insCdelT reversion mutation.

3. A mouse according to claim 1 wherein said mouse is a female mouse that has been backcrossed to C57BL/6J males.

4. A method for determining potential effectiveness of a candidate therapeutic in treating, delaying the onset of or lessening the severity of hypertrophic cardiomyopathy, said method comprising the steps of:
   A) providing a mouse according to claim 1;
   B) administering the candidate therapeutic to the mouse; and
   C) determining whether the candidate therapeutic was effective in treating, delaying the onset of or lessening the severity of hypertrophic cardiomyopathy, or of a symptom of hypertrophic cardiomyopathy, by comparing said mouse to one or more other mice according to claim 1 that was or were not administered the candidate therapeutic.

5. A method according to claim 4 wherein the candidate therapeutic comprises a drug.

6. A method according to claim 4 wherein the candidate therapeutic comprises a chemical composition.

7. A method according to claim 4 wherein the candidate therapeutic comprises a biologic.

8. A method according to claim 4 wherein the candidate therapeutic comprises a vaccine.

9. A method according to claim 4 wherein the candidate therapeutic comprises a therapeutic device.

* * * * *